US00PP20338P3

(12) United States Plant Patent

Dozier, Jr. et al.

(10) Patent No.: US PP20,338 P3

(45) Date of Patent: Sep. 22, 2009

(54) CHESTNUT PLANT NAMED 'AU GOBBLER I'

(50) Latin Name: *Castanea mollissima Blume*
Varietal Denomination: AU Gobbler I

(75) Inventors: W. Alfred Dozier, Jr., Opelika, AL (US); J. Daniel Norton, Auburn, AL (US); Curtis J. Hansen, Opelika, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 12/012,030

(22) Filed: Jan. 30, 2008

(65) Prior Publication Data

US 2009/0193549 P1 Jul. 30, 2009

(51) Int. Cl.
*A01H 5/00* (2006.01)

(52) U.S. Cl. ..... Plt./152

(58) Field of Classification Search ..... Plt./152
See application file for complete search history.

(56) References Cited

PUBLICATIONS

Lin ye ke ji et al., "Forest Science & Technology", Jan. 1989, pp. 16–18, Baker Auxiliary Stacks SD1. L56, No. 2–1990.*
Crane, H.L., et al., Nut Breeding, U.S. Department of Agriculture Yearbook, Jan. 1937, pp. 827–837.*
Hemming, E. Sam, "Chinese Chestnut In Maryland", Jan. 1944, pp. 32–34, A. R. Northern Nut Growers Assoc.*
Kim, Kap Duk et al., Studies on the Farmers Cultivating Chestnut Orchards In Korea And Its Financial Analysis, Jan. 1971, pp. 51–74, Bull. Seol. Nut. Univ. Fores., No. 8.*
Snare, Lester, Chestnuts Production, Jan. 1996, pp. 422–427, NSW Agriculture, Agfact H3.1.50., hhtp://www.r-irdc.gov.au/pub/handbook/chestnuts.pdf.*
Harris, Hubert et al., Three Chinese Chestnuts: Au–Cropper, Au–Leadder, And Au–Homestead—Their History And Production, Mar. 1980, pp. 3–8, Agricultural Experiment Station Auburn University Circular 247.*
Jaynes, Richard A. et al., "Handbook Of North Americna Nut Trees", pp. 264–286, the W.F. Humphrey Press, Inc. New York.*

* cited by examiner

*Primary Examiner*—Annette H Para
(74) *Attorney, Agent, or Firm*—Haverstock & Owens LLP

(57) ABSTRACT

'AU Gobbler I' is a new and distinct Chinese chestnut cultivar that is precocious and produces a large crop annually of small nuts that mature early and start dropping about August 25. Nut drop continues for a 4 to 5 week period. The nuts mature and start dropping 3–4 weeks before most cultivars. The early nut drop and small nut size of 'AU Gobbler I' makes it ideal for use as a food source for turkey and other wildlife species. 'AU Gobbler I' is an excellent companion cultivar to 'AU Gobbler II' as nut drop begins about 10 days earlier than nut drop of 'AU Gobbler II' and extends the season of available food supply for turkey and other wildlife. The major nut drop period of 'AU Gobbler I' occurs before the major nut drop period of 'AU Gobbler II'.

3 Drawing Sheets

Latin name of the genus and species of the plant claimed: *Castanea mollissima* Blume.
Variety denomination: 'AU Gobbler I'.

BACKGROUND OF THE INVENTION

A Chinese chestnut planting was established at Auburn University, Auburn, Ala., from nuts collected in China. The planting was established on the United States Department of Agriculture Horticulture Farm which in later years became the Mainstation Horticulture Farm. Precocious and prolific-bearing, blight resistant seedlings were selected for nut appearance, size and quality. Each generation of seedlings were the product of controlled mass pollination from the most promising seedlings selected from the previous generation. 'AU Cropper', 'AU Leader' and 'AU Homestead' were released from a second generation of approximately 2000 seedlings. A planting of third generation seedlings from controlled mass pollination of 'AU Leader', 'AU Homestead' and 'AU Cropper' was established at the Auburn University Piedmont Substation at Camp Hill, Ala.

SUMMARY OF THE INVENTION

'AU Gobbler I' is an open pollinated seedling of 'AU Leader'.

The present invention relates to a new and distinct Chinese chestnut cultivar that is precocious, produces a heavy crop annually, average nut size is small (7.7 g) and begins nut drop about August 25 and continues for a 4 to 5 week period. The nuts mature and start dropping 3–4 weeks before most chestnut cultivars. The large crop of small nuts produced by 'AU Gobbler I' chestnut is an excellent food source for turkey and other wildlife. Its small nut size is ideal for consumption by turkey. The plant has not been affected by chestnut gall wasp or chestnut blight.

'AU Gobbler I' is an excellent companion cultivar to 'AU Gobbler II' as nut drop begins about 10 days earlier than nut drop of 'AU Gobbler II' and extends the season of available food supply for turkey and other wildlife. 'AU Gobbler II' is disclosed in U.S. patent application Ser. No. 12/012,111, filed on Jan. 30, 2008, and entitled "CHESTNUT PLANT NAMED 'AU GOBBLER II'", which is hereby incorporated by reference.

The new cultivar is able to be asexually reproduced by budding or grafting onto a seedling Chinese chestnut rootstock. The unique characteristics come true to form and are established and transmitted through asexual propagation.

DETAILED BOTANICAL DESCRIPTION

Figure 1:
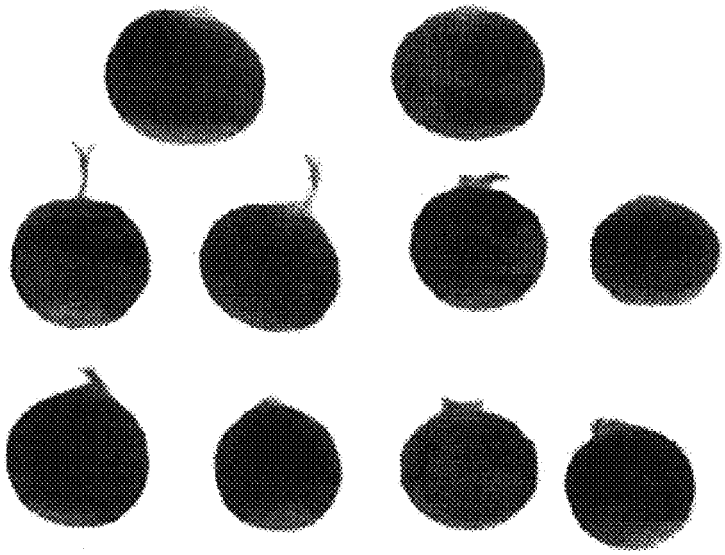
FIG. 1 is a photograph of nuts of the 'AU Gobbler I' cultivar.
Figure 2:
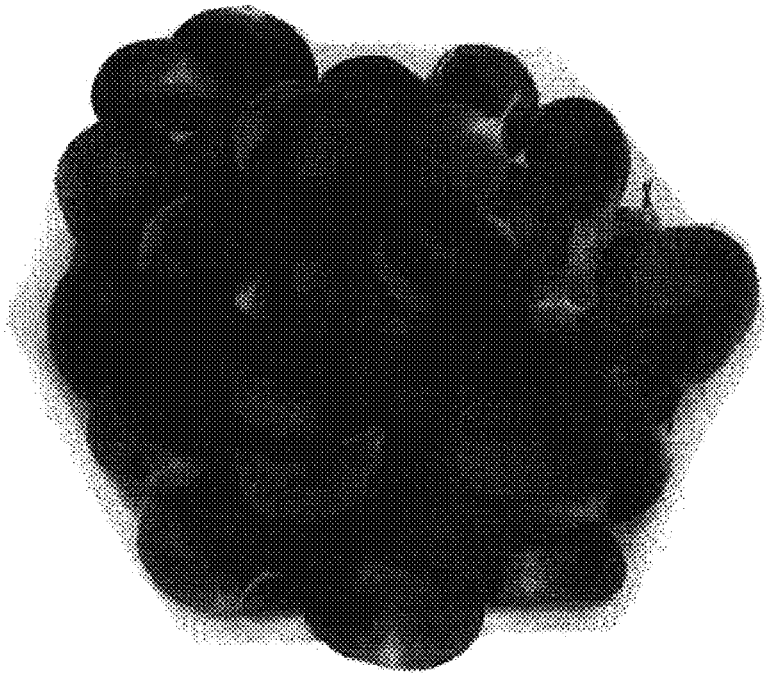
FIG. 2 is a photograph of nuts of the 'AU Gobbler I' cultivar.
Figure 3:
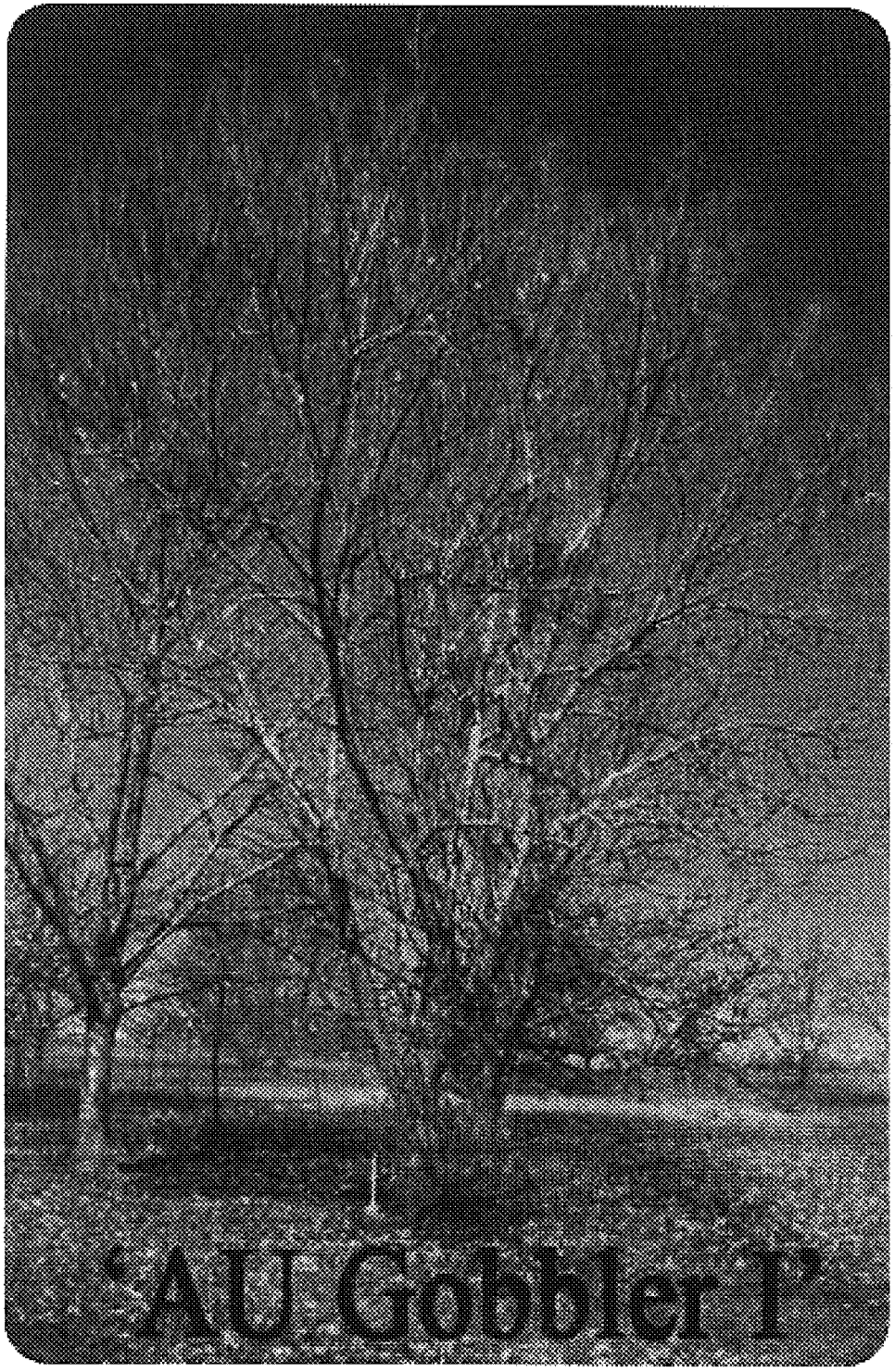
FIG. 3 is a photograph of a tree of the 'AU Gobbler I' cultivar.

The Chinese chestnut, *Castanea mollissima* Blume, is a cold hardy temperate zone species native to China. It can be grown between 30' and 50' latitudes. The Chinese chestnut is resistant to chestnut blight fungus *Cryphonectria parasitica.* Generally, Chinese chestnuts are grown on a wide range of soils, but well-drained, deep and fertile soils are considered the best. Soils should be slightly acidic with pH 5.6–6.5. The name *mollissima* means soft hair and this species is recognized by dense hair on young leaves and downy yellow terminal parts of the shoots in winter. The leaf blade is thicker, and, in general, mature leaves are broader than those of other species. The nuts have a small scar or hilum. The pellicle of thin membranous skin on the nuts is thin and peels readily from the kernel. The trees are spreading type and long lived with a round top. The trees have bark with furrows and buds with 3–4 scales and leaves are 2 ranked, serrated with numerous parallel veins.

Chestnuts are monoecious and staminate flowers appear on erect cylindrical catkins with 10–20 stamens and 6-parted calyx. Pistillate flowers are borne on the lower part of the upper staminate catkins and rarely on separate catkins, usually 3 in a prickly symmetrical involucre with 7–9 styles and a 6-celled ovary. Nuts are small, brown with a pale scar at the base. Generally, 1–3 nuts per involucre or bur are present.

The 'AU Gobbler I' cultivar is a tall upright tree. The overall tree shape is obovate, with diffuse and upright branches. The original 15-year old 'AU Gobbler I' tree is 10.97 m tall, has a diameter at breast height of 35.9 cm, canopy width of 10.11 meters and covers an area of 80.24 square meters. The 'AU Gobbler I' produces a small nut that has a 5-year average weight of 7.7 grams. The average nut length is 1.04 inches (26.4 mm) and average nut width is 1.22 inches (31.0 mm). The nuts ripen early, start dropping by about August 25 and continue to drop over a 4 to 5 week period. The nuts mature and start dropping 3–4 weeks before most cultivars. The tree started producing nuts the third year after planting, is very prolific and produces annually.

The early nut drop and small nut size of 'AU Gobbler I' makes it ideal for use as a food source for turkey and other wildlife. The small nut is excellent for turkeys to use as a high energy food source at a time when food is scarce in native woodlands.

In the planting at the Pidemont Substation, Camp Hill, Ala., accurate yields could not be obtained due to extremely heavy wildlife (deer and turkey) feeding. Therefore, the trees were rated for crop load each year and 'AU Gobbler I' has been rated as annual bearer of large crops each season. In the fall of 2006, individual trees were caged with 6 foot (1.83 m) tall chicken wire prior to nut drop to exclude wildlife and nuts were picked up daily from the beginning through completion of nut drop. The original 15-year old 'AU Gobbler I' tree produced 127 pounds (57.73 kg) of nuts in 2006. This is a higher yield than that reported by similar aged trees.

The table below illustrates the specific differences between the 'AU Gobbler I' cultivar and the 'Revival' cultivar.

---

The botanical details of this new and distinctive variety of chestnut tree - with color definitions (except those in common color terms) referenced to Royal Horticultural Society's Colour Chart (RHS) and color was also determined using an electronic spectrophotometer to determine hue angle and Chroma (spectrophotometer model CM-2002; Minolta Camera Co., Japan).

'AU GOBBLER 1' CHESTNUT

Tree:

Size (at maturity) - large - fifteen year old original tree is 10.97 meters tall with a canopy width of 10.11 meters and a canopy area of 80.24 sq. meters
Tree shape is obovate.
Vigor - very vigorous Trunk:

Form - upright, with branches high and diffuse
Texture - relatively smooth
Color of bark - greyed-green RHS 197A
Chroma C* 13.16, hue angle 77.24

Branches:

Form - upright
Texture - relatively smooth
Lenticels - few, small
Branching habit - high and diffuse, spreading in upper regions of tree.
Color - new wood: brown, RHS N200A, Chroma C* 10.21, hue angle 72.40; mature wood: greyed-green RHS 197A
Chroma C* 12.01, hue angle 88.37

Foliage:

Quantity - abundant
Density - dense

Leaves:

Size - large. Length (cm) 17.6 (14.2-24.3) [20]
width (cm) 6.5 (4.9-8.7) [20]
leaf ratio 2.8 (2.2-3.7) [20]
Shape - broadly elliptic to oblong
leaf tip- acute to occasionally acuminate
leaf base- rounded; oblique
Thickness- thick. Leaf venation 1* pinnate: 2* ± parallel, prominent abaxially
Texture - moderately coriaceous (thick)
Margin - coarsely serrate; teeth spreading
Petiole - length 0.8 cm (0.6-1.1) [20]
Petiole pubescence- glabrous to sparsely hairy
Color- adaxial surface, glabrous blade; glabrous veins, rarely with sparse simple hairs, dark green; moderately shiny, RHS 147A, Chroma C* 13.63, hue angle 122.39
abaxial surface, densely stellate hairs on blade; glabrous veins, light green RHS 147B, Chroma C* 17.47, hue angle 112.24

Bloom:

Amount of bloom - heavy
Color - at anthesis, RHS 161D greyed-yellow group, RHS 157D green-white group, RHS 155C white group
Blooming period - mid-May. After foliation in April.
Age at which tree starts flowering - early, 2-3 years after graft replacement.

The botanical details of this variety of chestnut tree-with color definitions (except those in common color terms) referenced to Maerz and Paul Dictionary of Color - are as follows:

'REVIVAL'

Tree:

Size (at maturity) - large
Vigor - very vigorous

Trunk:

Form - upright with branches spreading in upper reaches of tree.

-continued

Texture - relatively smooth
Color of bark - Silvergray (13-A-1)
Branches:

Form - strong
Texture - relatively smooth
Lenticels - few, small
Branching habit - spreading in upper region of tree
Color - new wood: reddish brown and glossy, mature wood: silver gray
Foliage:

Quantity - abundant
Density - dense
Leaves:

Size - large. Average length - 5-7" (including petiole).
Average width - 2"
Shape - oblong with acute tip and rounded base
Thickness - thick
Texture - smooth
Margin - dentate
Petiole - length: medium. Thickness: medium.
Color - Top side - glossy dark green (22-L-12).
Under side - lighter green (21-D-7).
Bloom:

Amount of bloom - heavy
Color - cream white (17-B-1)
Blooming period - late. After leaf out in April
Age at which tree starts flowering - early; 2-3 years years after graft replacement.
Male flower - Catkin length (cm) - 12.4 (9.4-15.4) [10]
Male flower - stamen number per catkin - 11.3 (10-13) [10]
Female flower - flower number per bur - 2.8
Female flower - style number per flower 8.4 (7-10) [11]
Crop:

Bearing - regular annual, bearer
Productivity - prolific
Ripening period - long, nuts begin dropping about August 25 and continue for a 4-5 week period.
Distribution of nuts on tree - well distributed, fruits on terminals with 2-4 burs per terminal.
Tenacity - burs crack while on tree and nuts release and drop from bur.
Hull:

Description - spiny, round bur
Size - 1.8-2.3" in diameter
Number of nuts - 2-3 per bur
Dehiscence - splits easily when still on tree
Color - yellow-green at dehiscence, RHS N144C
Nut:

Size - small; average size - 1.04" × 1.22" × 0.65". Average weight - 7.7 grams - 59 (53-90) nuts per pound.
Form - flattened on 1 side, occ.2; mostly hemispheric on other side; broadly rounded basally; rounded apically with a small tip.
Blossom end - small pointed tip
Basal end - flattened
Color - dark brown, lustrous; RHS 200B, Chroma C* 12.96, hue angle 38.86
Pubescence - mixed long and short, fine white hairs densely covering the distal
⅛ end of the nut, glabrous elsewhere
Shell - thin
Hardness of shell - relatively hard, yet not rigid
Texture of shell - smooth
Percentage of kernel to nut - very high - 90-95%
Kernel:

Size - almost as large as nut size
Form - same as nut shape
Pellicle - thin
Flavor - excellent, very sweet
Color - light straw color, RHS 153D, Chroma C* 53.46, hue angle 82.55
Resistance to insects: no unusual susceptibilities noted
Resistance to disease: no susceptibilities to disease noted -continued The chestnut tree and its nuts herein described may vary in slight detail due to climatic and soil conditions under which the variety may be grown; the present description being of the variety as grown in Camp Hill, Ala.
Crop:

Bearing - regular (yearly) bearer
Productivity - prolific
Ripening period - short. September 15-October 1.
Distribution of nuts on tree - well distributed
Tenacity - burrs crack while on tree and nuts easily release, many falling by themselves
Hull:

Description - spiny, round burr
Size - 3-4" in diameter
Number of nuts - 2-3 per burr
Dehiscence - splits easily when still on tree. Some entire burrs split and fall to ground
Color - brown (15-A-8)
Nut:

Size - large. Average size - 1⅛" × 1⅛" × 1" thick.
Average weight - 24-32 nuts per pound
Form - broad and ovoid on one side, flat on other side
Blossom end - pointed tip
Basal end - flattened
Color - India Red (7-L-6).
Shell - thin
Hardness of shell - relatively hard, yet not rigid
Texture of shell - smooth
Percentage of kernel to nut - very high (95%)
Kernel:

Size - almost as large as nut size
Form - same as nut shape
Pellicle - thin
Flavor - excellent. Very sweet.
Color - Oyster white (10-B-1)
Resistance to insects: no unusual susceptibilities noted
Resistance to disease: very high inherent resistance to chestnut bark fungus (*Endothia parastica*), no other susceptibilities to any other disease
The chestnut tree and its nuts herein described may vary in slight detail due to climatic and soil conditions under which the variety may be grown; the present description being of the variety as grown in Alachua, Fla.

'AU Buck I' is different from 'AU Gobbler I' in several ways. For example, the size of the trees, the trunk forms and colors, the branches, the leaves and the nuts have differences. Specifically, the 'AU Buck I' tree is shorter with a canopy width and canopy area much smaller than the 'AU Gobbler I' tree. The 'AU Buck I' branches are spreading, dense, low and grey-brown; whereas, the 'AU Gobbler I' branches are upright, high, diffuse and brown (new) or greyed-green (mature). The leaves differ in size, shape, texture, margin, petiole and color. The average weight of the nuts of 'AU Buck I' is 9.3 grams versus 7.7 grams for 'AU Gobbler I'. Furthermore, 'AU Buck I' has roughly 49 nuts per pound, and 'AU Gobbler I' has roughly 59 nuts per pound.

'AU Buck II' is different from 'AU Gobbler I' in several ways. For example, the size of the trees, the trunk forms and colors, the branches, the leaves, the crop and the nuts have differences. Specifically, the 'AU Buck II' tree is shorter with a canopy area larger than the 'AU Gobbler I' tree. The 'AU Buck II' branches are upright/spreading, low/spreading and brown (new) or grey-brown (mature); whereas, the 'AU Gobbler I' branches are upright, high, diffuse and brown (new) or greyed-green (mature). The leaves differ in size, shape, margin, petiole and color. The ripening period for the 'AU Buck II' is around September 14 and continues for a 4–5 week period, but the 'AU Gobbler I' ripening period is around August 25 and continues for 4–5 weeks. The average weight of the nuts of 'AU Buck II' is 16.6 grams versus 7.7 grams for 'AU Gobbler I'. Furthermore, 'AU Buck II' has roughly 27 nuts per pound, and 'AU Gobbler I' has roughly 59 nuts per pound.

'AU Buck III' is different from 'AU Gobbler I' in several ways. For example, the size of the trees, the trunk forms and colors, the branches, the leaves, the crop and the nuts have differences. Specifically, the 'AU Buck III' tree is shorter with a canopy area smaller than the 'AU Gobbler I' tree. The 'AU Buck III' branches are spreading and brown (new) or grey-brown (mature); whereas, the 'AU Gobbler I' branches are upright and brown (new) or greyed-green (mature). The leaves differ in size, petiole and color. The ripening period for the 'AU Buck III' is around September 25 and continues for a 4–5 week period, but the 'AU Gobbler I' ripening period is around August 25 and continues for 4–5 weeks. The average weight of the nuts of 'AU Buck III' is 10.9 grams versus 7.7 grams for 'AU Gobbler I'. Furthermore, 'AU Buck III' has roughly 42 nuts per pound, and 'AU Gobbler I' has roughly 59 nuts per pound.

'AU Buck IV' is different from 'AU Gobbler I' in several ways. For example, the size of the trees, the trunk forms and colors, the branches, the leaves, the crop and the nuts have differences. Specifically, the 'AU Buck IV' tree is shorter with a canopy width and a canopy area smaller than the 'AU Gobbler I' tree. The 'AU Buck IV' branches are upright to spreading and grey-brown (new) or greyed-green (mature); whereas, the 'AU Gobbler I' branches are upright and brown (new) or greyed-green (mature). The leaves differ in size, shape, texture, margin and color. The ripening period for the 'AU Buck IV' is around October 10 and continues for a 5–6 week period, but the 'AU Gobbler I' ripening period is around August 25 and continues for 4–5 weeks. The average weight of the nuts of 'AU Buck IV' is 15.5 grams versus 7.7 grams for 'AU Gobbler I'. Furthermore, 'AU Buck IV' has roughly 29 nuts per pound, and 'AU Gobbler I' has roughly 59 nuts per pound.

'AU Premier' is different from 'AU Gobbler I' in several ways. For example, the size of the trees, the branches, the leaves, the crop and the nuts have differences. Specifically, the 'AU Premier' tree is shorter with a canopy width and a canopy area smaller than the 'AU Gobbler I' tree. The 'AU Premier' branches are strong and low/dense/spreading; whereas, the 'AU Gobbler I' branches are upright and high/diffuse. The leaves differ in size, shape, thickness, texture, margin and color. The ripening period for the 'AU Premier' is early September through mid-November, but the 'AU Gobbler I' ripening period is around August 25 and continues for 4–5 weeks. The average weight of the nuts of 'AU Premier' is 1.26 grams versus 7.7 grams for 'AU Gobbler I'. Furthermore, 'AU Premier' has roughly 360.3 nuts per pound, and 'AU Gobbler I' has roughly 59 nuts per pound.

'AU Encore' is different from 'AU Gobbler I' in several ways. For example, the size of the trees, the branches, the leaves, the crop and the nuts have differences. Specifically, the 'AU Encore' tree is shorter with a canopy width and a canopy area smaller than the 'AU Gobbler I' tree. The 'AU Encore' branches are strong and low/dense/spreading; whereas, the 'AU Gobbler I' branches are upright and high/diffuse. The leaves differ in size, shape, thickness, texture, margin and color. The ripening period for the 'AU Encore' is late September through late November, but the 'AU Gobbler I' ripening period is around August 25 and continues for 4–5 weeks. The average weight of the nuts of 'AU Encore' is 2.4 grams versus 7.7 grams for 'AU Gobbler I'. Furthermore, 'AU Encore' has roughly 189.2 nuts per pound, and 'AU Gobbler I' has roughly 59 nuts per pound.

What is claimed is:

1. A new and distinct cultivar of the species *Castanea mollissima* Blume named 'AU Gobbler I' as described and illustrated herein.

* * * * *

'AU Gobbler I'

'AU Gobbler I'

UNITED STATES PATENT AND TRADEMARK OFFICE

CERTIFICATE OF CORRECTION

PATENT NO. : PP 20,338 P3
APPLICATION NO. : 12/012030
DATED : September 22, 2009
INVENTOR(S) : Dozier, Jr. et al.

It is certified that error appears in the above-identified patent and that said Letters Patent is hereby corrected as shown below:

At column 3, third line under the heading "DETAILED BOTANICAL DESCRIPTION", please replace "32'" and "50'" with "32°" and "50°" so that the sentence reads
-- It can be grown between 30° and 50° latitudes. --

At column 4, under the heading "Leaves:", please replace "1'" and "2'" with "1°" and "2°" so that the sentence reads
-- Thickness- thick. Leaf venation 1° pinnate: 2° ± parallel, prominent abaxially --

At column 5, under the heading "Nut:", please remove the line break after the word "distal" so that the sentence reads
-- Pubescence - mixed long and short, fine white hairs densely covering the distal 1/8 of the nut, glabrous elsewhere --

Signed and Sealed this

Third Day of November, 2009

David J. Kappos

David J. Kappos
*Director of the United States Patent and Trademark Office*